(12) United States Patent  
Wang et al.

(10) Patent No.: US 10,895,561 B2  
(45) Date of Patent: Jan. 19, 2021

(54) EMBEDDED SENSOR MODULE AND SENSING DEVICE

(71) Applicant: INDUSTRIAL TECHNOLOGY RESEARCH INSTITUTE, Hsinchu (TW)

(72) Inventors: Jung-Hao Wang, New Taipei (TW); Che-Hsin Lin, Kaohsiung (TW); Wei-Sin Kao, Kaohsiung (TW); Pai-Hao Wu, New Taipei (TW); Chen-Hua Chu, Zhubei (TW); Cheng-Hung San, Hsinchu County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 92 days.

(21) Appl. No.: 15/843,435

(22) Filed: Dec. 15, 2017

(65) Prior Publication Data

US 2019/0187112 A1 Jun. 20, 2019

(51) Int. Cl.
| | | |
|---|---|---|
| *G01N 33/00* | (2006.01) | |
| *G01F 1/684* | (2006.01) | |
| *G01N 33/18* | (2006.01) | |
| *G01N 27/06* | (2006.01) | |

(52) U.S. Cl.
CPC ....... *G01N 33/0027* (2013.01); *G01F 1/6842* (2013.01); *G01F 1/6845* (2013.01); *G01N 27/06* (2013.01); *G01N 33/18* (2013.01); *G01N 2291/02827* (2013.01)

(58) Field of Classification Search
CPC ............... G01N 33/0027; G01N 33/18; G01N 2291/02827; G01N 27/06; G01N 27/07; G01N 27/403; G01F 1/6842; G01F 1/6845
See application file for complete search history.

(56) References Cited

U.S. PATENT DOCUMENTS

| | | | |
|---|---|---|---|
| 4,348,905 A | | 9/1982 | Nishimura et al. |
| 4,624,770 A | * | 11/1986 | Yamada ............. G01N 27/4077 204/425 |
| 4,806,847 A | * | 2/1989 | Atherton ............... G01F 23/266 324/665 |
| 5,929,754 A | * | 7/1999 | Park ................... G01N 33/2888 324/663 |
| 6,419,807 B1 | | 7/2002 | Davies et al. |

(Continued)

FOREIGN PATENT DOCUMENTS

| | | |
|---|---|---|
| CN | 201803751 U | 4/2011 |
| CN | 202297600 U | 7/2012 |

(Continued)

OTHER PUBLICATIONS

Williams et al., "Multi-phase flow measurements in powder processing", Powder Technology, 66, (Jun. 1991), 203-224.

(Continued)

*Primary Examiner* — Randy W Gibson  
*Assistant Examiner* — Gedeon M Kidanu  
(74) *Attorney, Agent, or Firm* — Maschoff Brennan (57) ABSTRACT

An embedding sensor module includes a cylinder and at least one flake sensor. A fluid tank is surrounded by the cylinder. The cylinder has a plurality of orifice connected to the fluid tank. The flake sensor is embedded in the fluid tank.

13 Claims, 8 Drawing Sheets

(56) References Cited

U.S. PATENT DOCUMENTS

| | | | |
|---|---|---|---|
| 6,577,134 B2 | 6/2003 | Farruggia et al. | |
| 7,010,970 B2 | 3/2006 | Rediniotis et al. | |
| D551,182 S * | 9/2007 | Furukawa | D10/101 |
| 7,367,221 B2 | 5/2008 | Hintsche | |
| 7,735,354 B2 * | 6/2010 | Yamamoto | G01N 25/005 73/61.41 |
| 7,902,838 B2 * | 3/2011 | Stahlmann | G01F 23/268 324/658 |
| 2004/0129069 A1 * | 7/2004 | Sakawa | G01N 27/4077 73/114.32 |
| 2005/0150292 A1 * | 7/2005 | Yamamoto | G01N 27/226 73/304 R |
| 2006/0267785 A1 * | 11/2006 | Viscosi | G01F 23/268 340/623 |
| 2007/0169544 A1 * | 7/2007 | Yamamoto | G01N 25/005 73/61.41 |
| 2008/0038153 A1 * | 2/2008 | Yamamoto | G01F 23/268 422/82.12 |
| 2009/0090178 A1 * | 4/2009 | Sasanuma | G01F 23/266 73/295 |
| 2012/0001273 A1 | 1/2012 | Chen et al. | |
| 2013/0306475 A1 * | 11/2013 | Suzuki | G01N 27/4077 204/429 |
| 2016/0011159 A1 * | 1/2016 | Sekiya | G01N 33/0036 73/23.31 |
| 2016/0209346 A1 | 7/2016 | Brondum et al. | |

FOREIGN PATENT DOCUMENTS

| | | |
|---|---|---|
| CN | 203083619 U | 7/2013 |
| CN | 204115773 U | 1/2015 |
| CN | 204165567 U | 2/2015 |
| CN | 204374058 U | 6/2015 |
| CN | 204740153 U | 11/2015 |
| CN | 205483181 U | 8/2016 |
| CN | 205826284 U | 12/2016 |
| CN | 105568934 B | 5/2017 |
| CN | 106667194 A | 5/2017 |
| DE | 202013007756 U1 | 12/2013 |
| JP | H11-044669 A | 2/1999 |
| JP | 2011-017594 A | 1/2011 |
| KR | 100548507 B1 | 1/2006 |
| KR | 101127862 B1 | 3/2012 |
| TW | M311878 U | 5/2007 |
| TW | 201043809 A | 12/2010 |
| TW | M441751 U | 11/2012 |
| TW | M446333 U | 2/2013 |

OTHER PUBLICATIONS

Silpa Mohan P M1, M Jeena Poomima, "Smart Real-Time Pipeline Inspection and Contamination Detection in Drinking Water Distribution System", International Journal of Engineering Science and Computing, May 2016,5634-5638.

* cited by examiner

EMBEDDED SENSOR MODULE AND SENSING DEVICE

TECHNICAL FIELD

The disclosure relates to an embedded-type sensing module and a sensing device, more particularly to an embedded-type sensing module and a sensing device having a plate-shaped sensor.

BACKGROUND

With raising awareness of environmental protection, there is an increasing demand on detecting ionic concentration, temperature, pH value, electric conductivity, light transmittance, turbidity, biochemical oxygen demand (BOD) and content of specific molecules of flowing fluid in pipes in order to make sure the properties and composition of the fluid to meet the requirements.

At this stage, the properties and compositions of the fluid in the pipes are obtained by an off-line or an online measuring method. The so-called off-line measuring method is to sample the fluid by disposing a branch pipe and then to analyze the fluid sample in labs. However, before analyzing the sample, time has passed for a while, so the result is not real time data. In addition, during delivery, the fluid sample may expose to environment and get contaminated, resulting in an inaccurate result. Therefore, the online measuring method is used more often.

In a conventional online measuring method, its sensing module is directly disposed in the pipe where the fluid flows. However, one sensor is only able to measure one property of the fluid at a time while using conventional sensors. To measure different properties of the fluid at the same time, various types of sensors are required to be placed into the pipe, but this increases the overall size of the sensor module and makes it not easy to be constructed as a disposable sensor module.

SUMMARY OF THE INVENTION

The disclosure provides an embedded-type sensing module and a sensing device, which are capable of solving the aforementioned problems that the sensor modules are too large and too expensive to be disposed.

One embodiment of the disclosure provides an embedded-type sensing module includes a tank and at least one plate-shaped sensor. The tank surrounds and defines a fluid chamber, and the tank has a plurality of through holes. The through holes are connected to the fluid chamber. The at least one plate-shaped sensor is embedded in the fluid chamber.

One embodiment of the disclosure provides a sensing device includes a pipe, a tank and at least one plate-shaped sensor. The pipe surrounds and defines a fluid channel. The tank surrounds and defines a fluid chamber. The tank has a plurality of through holes and the through holes are connected to the fluid chamber. The at least one plate-shaped sensor is embedded in the fluid chamber. The tank is detachably plugged into the pipe, such that the at least one plate-shaped sensor is connected to the fluid channel through the through holes.

The aforementioned summary and the following detailed description are set forth in order to provide a thorough understanding of the disclosed embodiment and provide a further explanations of claims of the disclosure.

DETAILED DESCRIPTION

Figure 1:
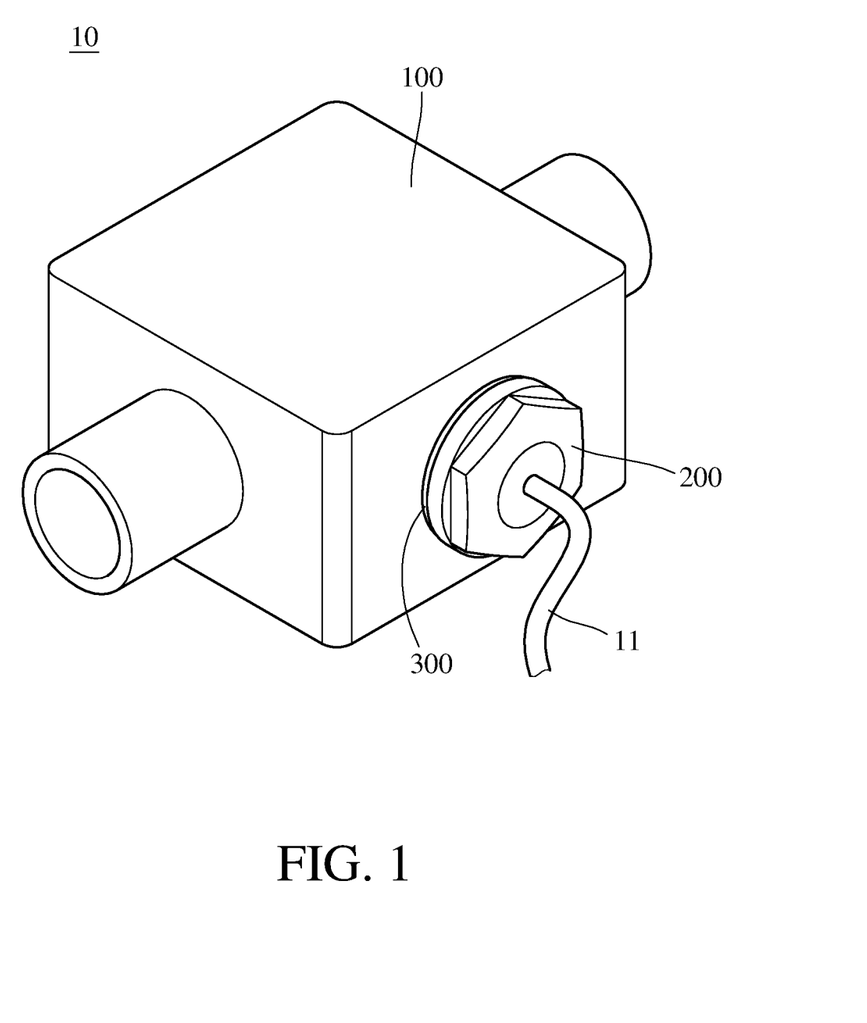
FIG. 1 is a perspective view of a sensing device according to a first embodiment of the disclosure.
Figure 2:
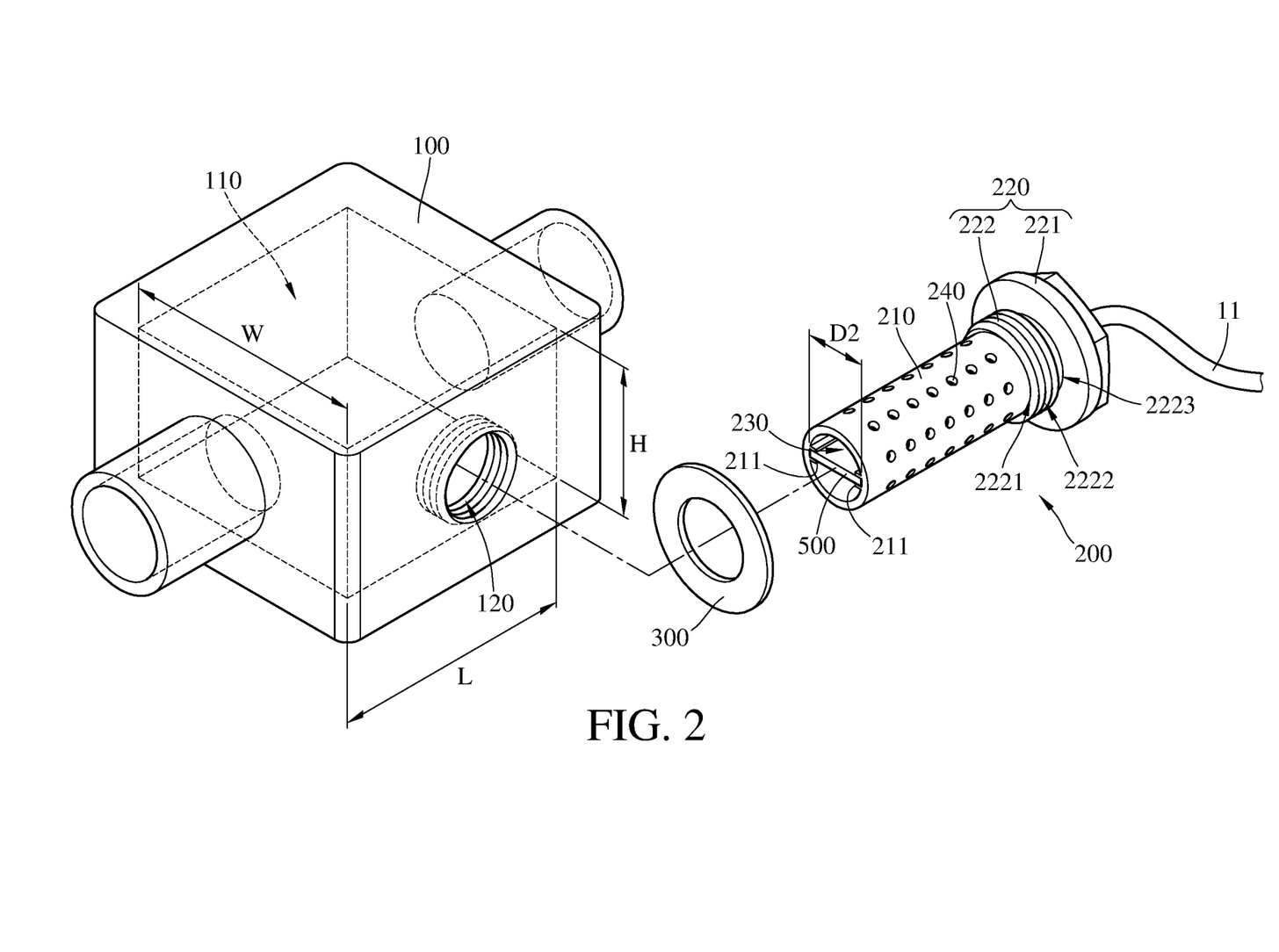
FIG. 2 is an exploded view of the sensing device in FIG. 1.
Figure 3:
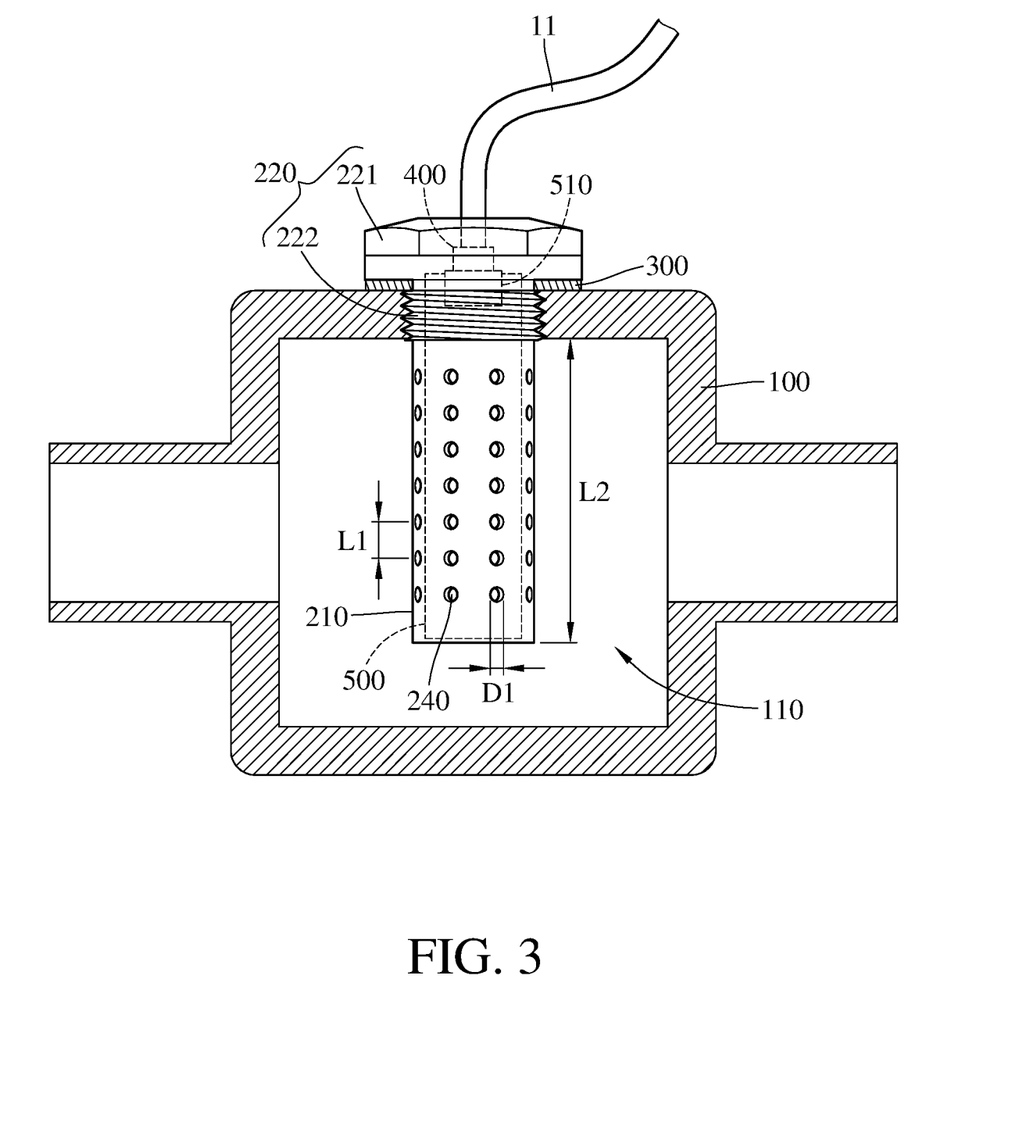
FIG. 3 is a cross-sectional view of the sensing device in FIG. 1.

Please refer to FIG. 1 to FIG. 3. FIG. 1 is a perspective view of a sensing device according to a first embodiment of the disclosure. FIG. 2 is an exploded view of the sensing device in FIG. 1. FIG. 3 is a cross-sectional view of the sensing device in FIG. 1.

The sensing device 10 of this embodiment, for example, is configured to measure ionic concentration, temperature, PH value, electric conductivity, light transmittance, turbidity, biochemical oxygen demand and content of specific molecules of fluid in a pipe 100.

The sensing device 10 includes a pipe 100, a tank 200, a sealing ring 300, a first electrical connector 400 and a plate-shaped sensor 500. The pipe 100 surrounds a fluid channel 110 for the fluid to flow therethrough. The pipe 100 has an internal thread 120 for the assembly of the tank 200 which will be described later. The plate-shaped sensor 500 is able to be embedded in the tank 200 to form an embedded-type sensing module.

The tank 200 surrounds and defines a fluid chamber 230, and the tank 200 has a plurality of through holes 240 connected to the fluid chamber 230. In detail, the tank 200 includes a cylinder portion 210 and a mounting portion 220 connected to each other in an axial direction of the tank 200.

The cylinder portion 210 surrounds the fluid chamber 230, and the through holes 240 are located at the cylinder portion 210. The cylinder portion 210 has two guiding slots 211, and the two guiding slots 211 are both located in the fluid chamber 230. The two guiding slots 211 respectively extend from an end of the cylinder portion 210 far away from the mounting portion 220 to the mounting portion 220. The mounting portion 220 includes a base part 221 and a ring part 222, and the ring part 222 protrudes from the base part 221. The cylinder portion 210 is connected to a side of the ring part 222 far away from the base part 221. The ring part 222 has an outer surface 2221 and an external thread 2222, and the external thread 2222 is located at the outer surface 2221. The tank 200 is detachably plugged into the pipe 100, and the external thread 2222 of the ring part 222 is engaged with the internal thread 120 of the pipe 100 so that the tank 200 is able to be fixed to the pipe 100.

The ring part 222 further has a groove 2223 located on the outer surface 2221, and the groove 2223 is located between the external thread 2222 and the base part 221. The sealing ring 300 is sleeved in the groove 2223 and clamped between the base part 221 and the pipe 100 so as to prevent the fluid from leaking from the junction of the base part 221 of the tank 200 and the pipe 100. The first electrical connector 400 is disposed in the base part 221 of the mounting portion 220, and two opposite ends of the plate-shaped sensor 500 respectively corresponded to the two guiding slots 211 and are guided by the two guiding slot 211 so that the plate-shaped sensor 500 can be embedded into the fluid chamber 230 and connected to the fluid channel 110 through the through holes 240. The plate-shaped sensor 500 has a second electrical connector 510, and the second electrical connector 510 is electrically connected to the first electrical connector 400.

In this embodiment, the plate-shaped sensor 500 is produced through a micromachining fabrication process and screen-printed electrodes technique, and the plate-shaped sensor 500 is, for example, a sensor that is able to measure one property of fluid, or a sensor that is able to measure multiple properties of fluid at a time. In addition, the first electrical connector 400 is waterproof packaged and then embedded into the base part 221 of the mounting portion 220, and an electrical wire 11 is penetrated an end of the base part 221 far away from the cylinder portion 210 to electrically connect to the first electrical connector 400 so as to provide electricity that the plate-shaped sensor 500 requires and to deliver signals that the plate-shaped sensor 500 senses.

In this embodiment, the structure and the through holes 240 of the tank 200 help to mitigate the speed and the pressure of the fluid which flows in the pipe 100, such that the speed and the pressure of the fluid entering into the fluid chamber 230 through the through holes 240 are decreased, thereby making the fluid become a steady flow field so as to prevent the plate-shaped sensor 500 from broken as well as enhance the numerical values stability and the accuracy in measuring the properties and compositions of the fluid. In addition, the adjustments of the diameters D1 of the through holes 240, the inner diameter D2 of the tank 200, the gap L1 between two of the through holes 240 adjacent to each other in the axial direction of the tank 200, and the pipe length L2 of the cylinder portion 210 are able to further decrease the speed and the pressure in the fluid chamber 230 of the tank 200. The following presents the detailed descriptions thereof.

Figure 4:
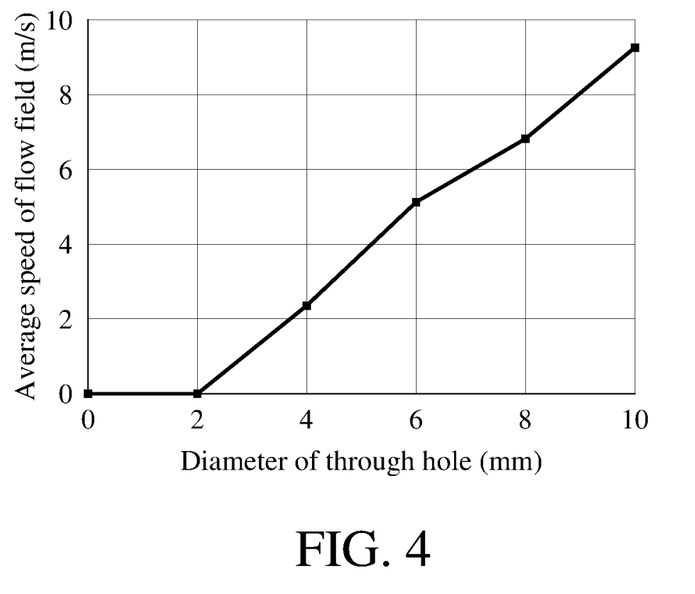
FIG. 4 is a broken line graph showing the variation of the average speed of the flow field in the fluid chamber under a condition that the through holes in FIG. 3 are different in diameters.
Figure 5:
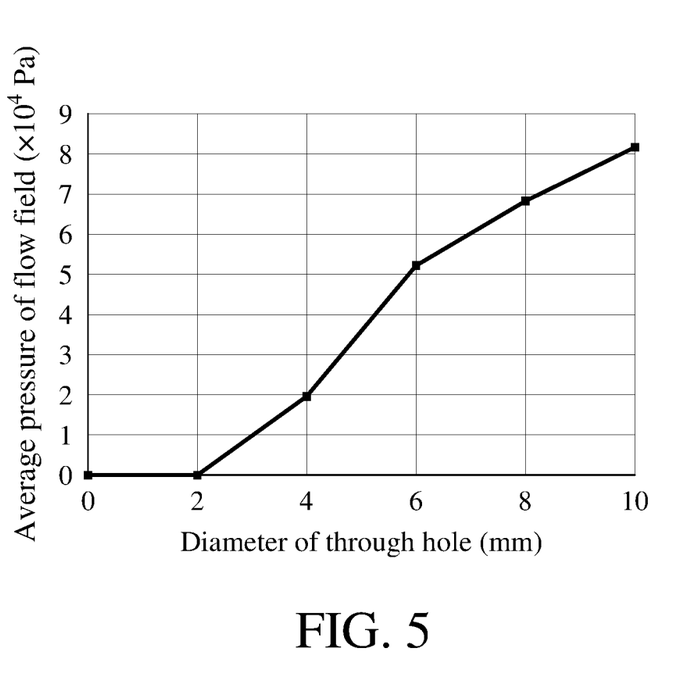
FIG. 5 is a broken line graph showing the variation of the average pressure of the flow field in the fluid chamber under the condition that the through holes in FIG. 3 are different in diameters.

Firstly, the relationship between the diameter D1 of the through hole 240 and the inner diameter D2 of the tank 200 are illustrated by simulation experiments. Please refer to FIG. 4 and FIG. 5. FIG. 4 is a broken line graph showing the variation of the average speed of the flow field in the fluid chamber under a condition that the through holes in FIG. 3 are different in diameters. FIG. 5 is a broken line graph showing the variation of the average pressure of the flow field in the fluid chamber under the condition that the through holes in FIG. 3 are different in diameters.

In an simulation experiment, the inner diameter D2 of the tank 200 is 50 mm, the length L2 of the cylinder portion 210 is 100 mm, the gap L1 between two adjacent through holes 240 in the axial direction of the tank 200 is 20 mm, the length L, the width W, and the height H of the flow field are respectively 300 mm, 100 mm, and 100 mm, the inlet speed of the flow field is 10 m/s, and the viscosity of the fluid is $1 \times 10^{-3}$ Pa·S, under such environment, the variations of the speed and the pressure are observed in the condition that the through holes 240 are different in diameter.

As shown in FIG. 4 and FIG. 5, as the diameter D1 of the through hole 240 increases from 2 mm to 10 mm, the speed and the pressure of the fluid in the fluid chamber 230 increase with the increase of the diameter D1 of the through hole 240. Among them, when the diameter of the through hole 240 is smaller than 2 mm, the speed and the pressure of the fluid in the fluid chamber 230 are 0, which means that the fluid does not flow into the fluid chamber 230. Then, when the diameter D1 of the through hole 240 is 6 mm, the speed of the fluid in the fluid chamber 230 is decreased from 10 m/s to 5.12 m/s, and the pressure of the fluid in the fluid chamber 230 is decreased from about $8.20 \times 10^4$ Pa to $5.23 \times 10^4$ Pa, which means that the through holes 240 of this size helps to effectively decrease the speed and the pressure of the fluid in the fluid chamber 230. However, when the diameter D1 of the through hole 240 is 10 mm, the speed and the pressure of the fluid in fluid chamber 230 are almost equal to that at the inlet of the flow field, which means that the through holes 240 are too large in size so that there is no obvious effect on decreasing the speed and the pressure. Thus, when the ratio of the diameter D1 of the through hole 240 to the inner diameter D2 of the tank 200 is between one-tenth and one-fifth, it is able to effectively decrease the speed and the pressure of the fluid in the fluid chamber 230.

Figure 6:
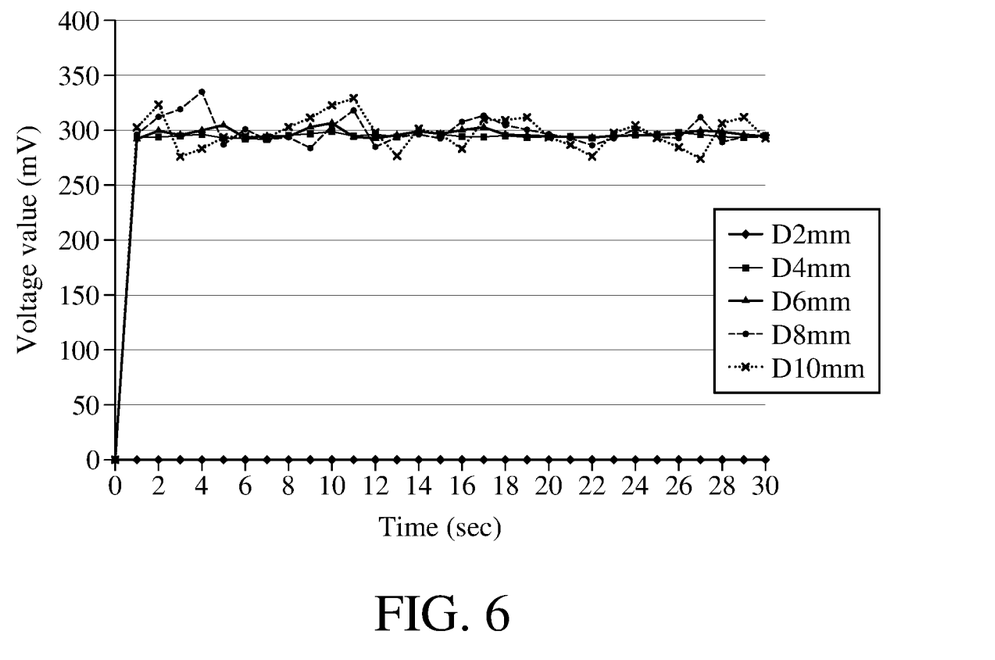
FIG. 6 is a broken line graph showing the variation of the voltage value measured by the plate-shaped sensor over time under the condition that the through holes in FIG. 3 are different in diameters.
Figure 7:
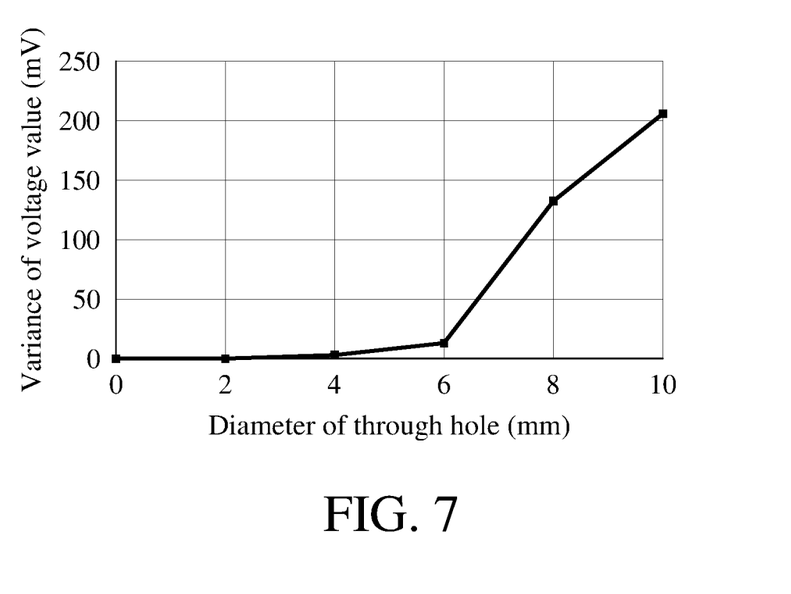
FIG. 7 is a broken line graph showing the variance of the voltage value measured by the plate-shaped sensor under the condition that the through holes in FIG. 3 are different in diameters.

Then, through the electric conductivity and the voltage value of a known fluid, it is able to determine, under the condition that the through holes 240 are different in diameter D1, the influence of the flow field of the fluid chamber 230 on the voltage value sensed by the plate-shaped sensor 500. Please refer to FIG. 6 and FIG. 7. FIG. 6 is a broken line graph showing the variation of the voltage value measured by the plate-shaped sensor over time under the condition that the through holes in FIG. 3 are different in diameters. FIG. 7 is a broken line graph showing the variance of the voltage value measured by the plate-shaped sensor under the condition that the through holes in FIG. 3 are different in diameters.

For example, if the electric conductivity of the fluid is 0.748 mS/cm, and the voltage value of the fluid in a resting state is 296 mV. Under the conditions same as the previous simulation, when the fluid is flowing in the fluid chamber 230, the voltage value measured by the plate-shaped sensor 500 at different time would change over time with the increase of the diameters D1 of the through holes 240, and the variance of the voltage would be increased with the increase of the diameter D1 of the through hole 240. In detail, as shown in FIG. 6 and FIG. 7, when the diameter D1 of the through hole 240 is smaller than 2 mm, the variance of the voltage is 0 because the speed of the fluid in the fluid chamber 230 is 0. When the diameter D1 of the through hole 240 is 10 mm, the speed of the fluid in the fluid chamber 230 approximately equals to the inlet speed of the flow field, thus the plate-shaped sensor 500 would be disturbed and effected by the flowing fluid and the variation of the pressure, such that the voltage value would change over time, and the variance of the voltage value may go up to 206 mV. Accordingly, when the fluid is flowing in the fluid chamber 230, the ratio of the diameters D1 of the through holes 240 to the inner diameter D2 of the tank 200 ranging between one-tenth and one-fifth helps to decrease the speed and the pressure of the fluid in the fluid chamber 230 and to maintain the variance of the voltage value in a low level.

Figure 8:
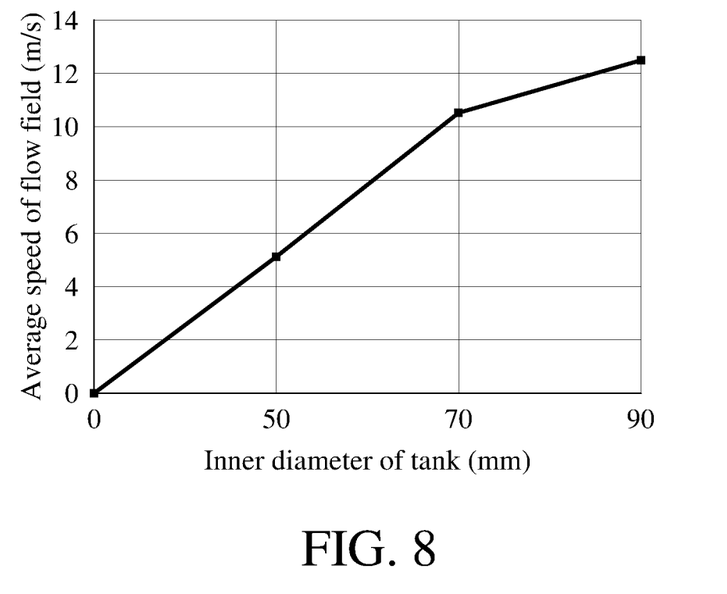
FIG. 8 is a broken line graph showing the average speed of the flow field in the fluid chamber under a condition that the inner diameters of the tank in FIG. 2 are different in size.
Figure 9:
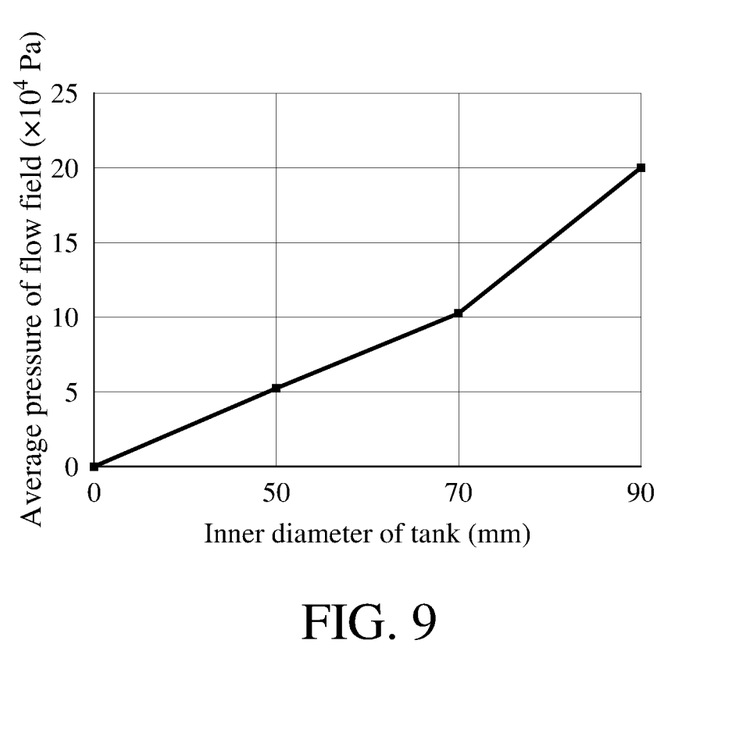
FIG. 9 is a broken line graph showing the average pressure of the flow field in the fluid chamber under the condition that the inner diameters of the tank in FIG. 2 are different in size.

Through the aforementioned simulations and experiments, it is understood that the diameter D1 of the through hole 240 being in 6 mm can not only effectively decrease the speed and the pressure of the fluid in the fluid chamber 230, but also maintain the variance of the plate-shaped sensor 500 in an acceptable range. Then, to simulate the influence of the inner diameter D2 of different size on the speed and the pressure of the fluid in the fluid chamber 230 under a condition that the diameter D1 of the through hole 240 is fixed in 6 mm but other conditions are unchanged. FIG. 8 is a broken line graph showing the average speed of the flow field in the fluid chamber under a condition that the inner diameters of the tank in FIG. 2 are different in size. FIG. 9 is a broken line graph showing the average pressure of the flow field in the fluid chamber under the condition that the inner diameters of the tank in FIG. 2 are different in size.

As shown in FIG. 8 and FIG. 9, when the inner diameters D2 of the tank 200 are 70 mm and 90 mm, the speeds of the fluid in the fluid chamber 230 are respectively 10.53 m/s and 12.5 m/s, and the fluid pressures are respectively $10.25 \times 10^4$ Pa and $20 \times 10^4$ Pa. That is, with the increase of the inner diameter D2 of the tank 200, the speed and the pressure of the fluid in the fluid chamber 230 increase. Among them, when the inner diameter D2 of the tank 200 is 70 mm, the speed of the fluid in the fluid chamber 230 is close to the inlet speed of the flow field. Moreover, when the inner diameter D2 of the tank 200 goes up to 90 mm, the speed of the fluid in the fluid chamber 230 exceeds the inlet speed of the flow field. Therefore, the variances, under conditions that the inner diameters D2 of the tank 200 are 70 mm and 90 mm, are greater than the variance, under the condition that the inner diameter D2 of the tank is 50 mm. The aforementioned simulations and experiments are able to verify that the ratio of the diameter D1 of the through hole 240 to the inner diameter D2 of the tank 200 ranging between one-tenth and one-fifth helps to further decrease the speed and the pressure of the fluid in the fluid chamber 230 so as to obtain a smaller variance and to improve the accuracy of the plate-shaped sensor 500.

Figure 10:
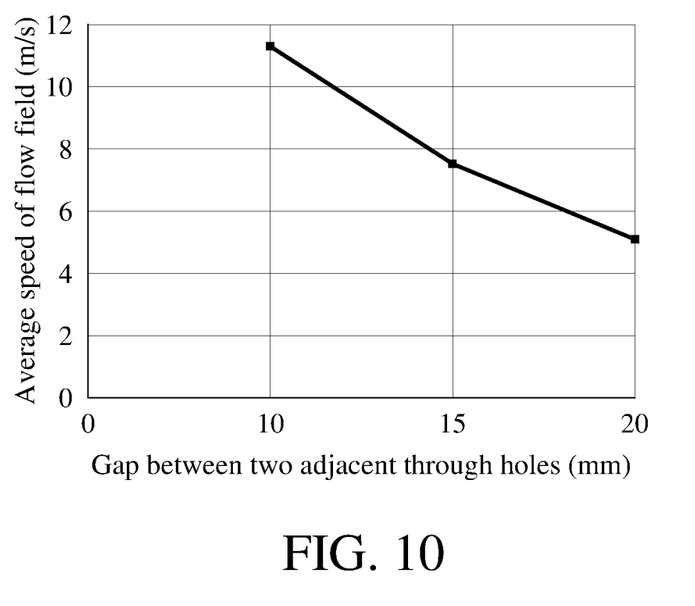
FIG. 10 is a broken line graph showing the average speed of the flow field in the fluid chamber under a condition that the gap between two adjacent through holes in the axial direction of the tank in FIG. 3 changes.
Figure 11:
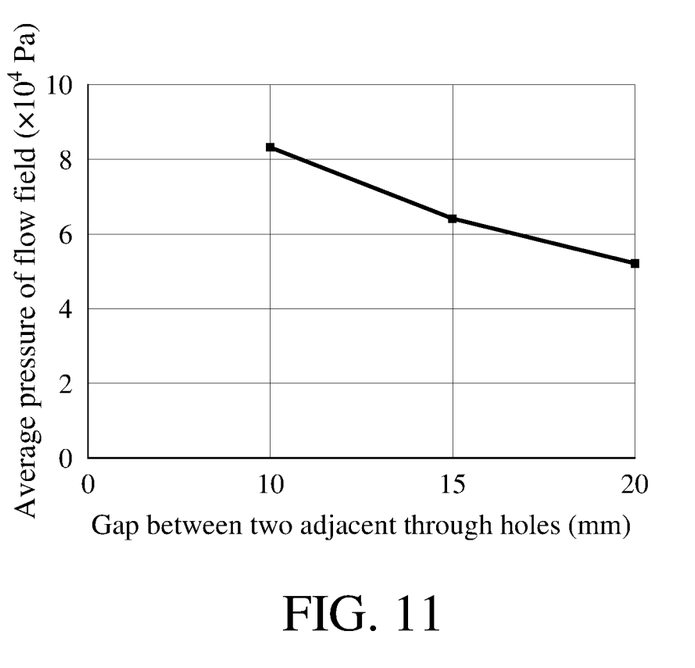
FIG. 11 is a broken line graph showing the average pressure of the flow field in the fluid chamber under the condition that the gap between two adjacent through holes in the axial direction of the tank in FIG. 3 changes.

Then, the relationship between the gap L1 between two adjacent through holes 240 in the axial direction of the tank 200 and the pipe length L2 of the cylinder portion 210 is illustrated by other simulation experiments. Please refer to FIG. 10 and FIG. 11. FIG. 10 is a broken line graph showing the average speed of the flow field in the fluid chamber under a condition that the gap between two adjacent through holes in the axial direction of the tank in FIG. 3 changes. FIG. 11 is a broken line graph of average pressure of flow field in the fluid chamber under the condition that the gap between two adjacent through holes in the axial direction of the tank in FIG. 3 changes.

In an simulation experiment, the inner diameter D2 of the tank 200 is 50 mm, the pipe length L2 of the cylinder portion 210 is 100 mm, the diameter D1 of the through holes 240 is 20 mm, the length L, the width W, and the height H of the flow field are respectively 300 mm, 100 mm, and 100 mm, the inlet speed of the flow field is 10 m/s, and the viscosity of the fluid is $1 \times 10^{-3}$ Pa·S, under such environment, the variations of the speed and the pressure are observed in the condition that the gaps L1 between two adjacent through holes 240 in the axial direction of tank 200 changes.

As shown in FIG. 10 and FIG. 11, as the gap L1 between two adjacent through holes 240 increases, the speed and the pressure of the fluid in the fluid chamber 230 are gradually decreased. In detail, when the gap L1 between two adjacent through holes 240 in the axial direction of the tank 200 is 10 mm, the speed of the fluid in the fluid chamber 230 is 11.32 m/s, having no effect on decreasing the inlet speed of the flow field. When the gap L1 between two adjacent through holes 240 in the axial direction of the tank 200 is 15 mm, the speed of the fluid in the fluid chamber 230 is 7.53 m/s, having an obvious effect on decreasing the inlet speed of the flow field. Thus, when the ratio of the gap L1 between two adjacent through holes 240 in the axial direction of the tank 200 to the pipe length L2 of the cylinder portion 210 is greater than one-tenth, it helps to further decrease the speed and the pressure of the fluid in the fluid chamber 230.

In this embodiment, the aforementioned simulations and the experiments show that the ratio of the diameters D1 of the through holes 240 to the inner diameter of the tank D2 is required to be between one-tenth and one-fifth, and the ratio of the gap L1 between two adjacent through holes 240 in the axial direction of the tank 200 to the pipe length L2 of the cylinder portion 210 is required to be greater than one-tenth, and it helps to further decrease the speed and the pressure of the fluid in the fluid chamber 230 so as to form a steady and smooth flow field, thereby not only improving the measuring accuracy and numerical values stability, but also preventing the sensing device 10 from broken while the plate-shaped sensor 500 measuring the properties and the compositions of the fluid.

In addition, in the aforementioned simulations and experiments, the diameters D1 of the through holes 240 of the cylinder portion 210 are the same, but the present disclosure is not limited thereto. In some other embodiments, the through holes on the same cylinder portion may be different in size under the condition that the ratio of the diameter of the through hole to the inner diameter of the tank is required to be between one-tenth and one-fifth, and the ratio of the gap between two adjacent through holes in the axial direction of the tank to the pipe length of the cylinder portion is required to be greater than one-tenth.

Figure 12:
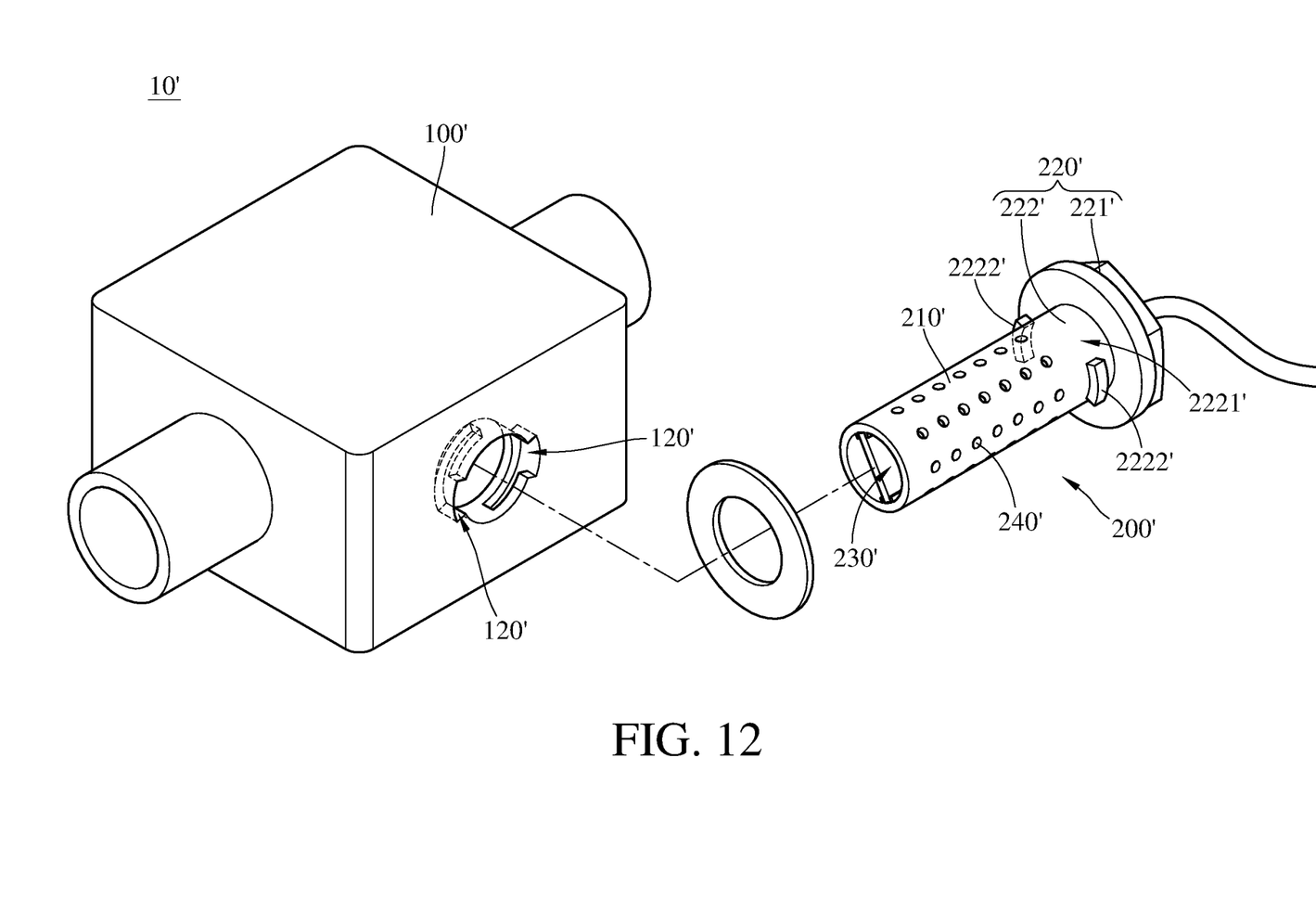
FIG. 12 an exploded view of a sensing device according to a second embodiment of the disclosure.

Furthermore, in this embodiment, the tank 200 is firmly fixed on the pipe 100 through the engagement of the external thread 2222 of the ring part 222 and the internal thread 120 of the pipe 100, such that the tank 200 is not able to be moved by the pressure of the fluid, thereby ensuring the measuring accuracy and stability. Moreover, the tank 200 is engaged on the pipe 100 through the threads, but the present disclosure is not limited thereto. Please refer to FIG. 12. FIG. 12 an exploded view of the sensing device according to a second embodiment of the disclosure.

In the sensing device 10' of this embodiment, the tank 200' surrounds and defines a fluid chamber 230', and the tank 200' has a plurality of through holes 240' which are connected to the fluid chamber 230'. In detail, the tank 200' includes a cylinder portion 210' and a mounting portion 220' connected to each other in an axial direction. The cylinder portion 210' surrounds the fluid chamber 230', and the through holes 240' are located on the cylinder portion 210'. The mounting portion 220' includes a base part 221' and a ring part 222'.

The ring part 222' protrudes from the base part 221', and the cylinder portion 210' is connected to a side of the ring part 222' far away from the base part 221'. The ring part 222' has an outer surface 2221' and a first fastening structure 2222', and the first fastening structure 2222' is located on the outer surface 2221'. The pipe 100' has a second fastening structure 120', and the first fastening structure 2222' is fixed in the second fastening structure 120' so as to fix the tank 200' to the pipe 100'. In this embodiment, the quantities of the first fastening structure 2222' and the second fastening structure 120' are both two, but the present disclosure is not limited thereto.

According to the sensing device as discussed above, to measure multiple properties of the fluid at the same time, it only needs to put one or more sensing elements, which can respectively measure different properties of the fluid, on the plate-shaped sensor, such that the total weight and size of the plate-shaped sensor would not be largely increased, so the plate-shaped sensor is still easily be disposed in the pipe.

In addition, by disposing the plate-shaped sensor in the fluid chamber of the tank, the structure and the through holes of the tank are able to mitigate the speed and the pressure of the flowing fluid in pipe while the fluid flowing into the fluid chamber through the through hole, such that the speed and the pressure of the fluid flowing into the fluid chamber are decreased so as to form a steady flow field, thereby preventing the plate-shaped sensor from broken, and enhancing the numerical values stability and the accuracy in measuring the properties and the compositions of the fluid.

Moreover, the ratio of the diameter of the through hole to the inner diameter of the tank being between one-tenth and one-fifth, and the ratio of the gap between two adjacent through holes in the axial direction of the tank to the pipe length of the cylinder portion being greater than one-tenth both help to further decrease the speed and the pressure of the fluid in the fluid chamber so as to form a steady and smooth flow field, thereby not only increasing the measuring accuracy and the numerical values stability, but also preventing the sensing device from being broken while the plate-shaped sensor measuring the properties and the compositions of the fluid.

In addition, the tank may be mounted on the pipe through threads or fastening structures, such that the tank can be firmly fixed on the pipe. Thus, the tank is not able to be moved by the pressure of the fluid so as to maintain the measuring accuracy and stability of the plate-shaped sensor.

It will be apparent to those skilled in the art that various modifications and variations can be made to the present disclosure. It is intended that the specification and examples be considered as exemplary embodiments only, with a scope of the disclosure being indicated by the following claims and their equivalents.

Symbol Description 10, 10' sensing device
11 electrical wire
100, 100' pipe
110 fluid channel
120 internal thread
120' second fastening structure
200, 200' tank
210, 210' cylinder portion
211 guiding slot
220, 220' mounting portion
221, 221' base part
222, 222' ring part
2221, 2221' outer surface
2222 external thread
2222' first fastening structure
2223 groove
230, 230' fluid chamber
240, 240' through hole
300 sealing ring
400 first electrical connector
500 plate-shaped sensor
510 second electrical connector
D1 diameter
D2 inner diameter
L2 pipe length
L1 gap
L length
W width
H height

What is claimed is:

1. A sensing module, comprising:
   a hollow component comprising a cylinder portion surrounding and defining a fluid chamber, the hollow component comprising a plurality of through holes located on the cylinder portion and connected to the fluid chamber; and
   at least one plate-shaped sensor embedded in the fluid chamber, wherein the hollow component comprises two guiding slots in the fluid chamber, and two opposite sides of the plate-shaped sensor are respectively directly positioned in the guiding slots;
   wherein a diameter of each of the plurality of through holes and an inner diameter of the hollow component have a ratio between one-tenth and one-fifth, and the hollow component includes an opening at a distal end thereof;
   wherein the plate-shaped sensor extends to the opening at the distal end of the hollow component and is exposed by the opening, and
   wherein a gap between two of the plurality of through holes adjacent to each other in the axial direction of the hollow component and a length of the cylinder portion have a ratio greater than one-tenth.

2. The sensing module according to claim 1, wherein the plurality of through holes comprise different diameters.

3. The sensing module according to claim 1, wherein the hollow component comprises a mounting portion connected to the cylinder portion each other in an axial direction of the hollow component.

4. The sensing module according to claim 3, further comprises a sealing ring, the mounting portion comprises a base part and a ring part, the ring part protrudes from the base part, the cylinder portion is connected to a side of the ring part opposite to the base part, the ring part comprises an outer surface, a groove and an external thread, the groove and the external thread are both located on the outer surface, the groove is located between the external thread and the base part, and the sealing ring is sleeved in the groove.

5. The sensing module according to claim 3, further comprises a first electrical connector, the at least one plate-shaped sensor comprises a second electrical connector, the first electrical connector is disposed in the mounting portion and electrically connected to the second electrical connector of the at least one plate-shaped sensor.

6. The sensing module according to claim 3, wherein the cylinder portion comprises the two guiding slots, the two guiding slots respectively extend from an end of the cylinder portion opposite to the mounting portion to the mounting portion.

7. The sensing module according to claim 3, wherein the mounting portion comprises a base part and a ring part, the ring part protrudes from the base part, the cylinder portion is connected to a side of the ring part opposite to the base part, the ring part comprises an outer surface and a fastening structure, and the fastening structure is located on the outer surface.

8. A sensing module, comprising:
  a hollow component surrounding and defining a fluid chamber, the hollow component comprising a plurality of through holes, and the plurality of through holes connected to the fluid chamber; and
  at least one plate-shaped sensor embedded in the fluid chamber;
  wherein a diameter of each of the plurality of through holes and an inner diameter of the hollow component have a ratio between one-tenth and one-fifth, and the hollow component includes an opening at a distal end thereofexposing the plate-shaped sensor; and
  wherein a gap between two of the plurality of through holes adjacent to each other in the axial direction of the hollow component and a length of the cylinder portion have a ratio greater than one-tenth.

9. A sensing device, comprising:
  a pipe surrounding and defining a fluid channel;
  a hollow component comprising a cylinder portion surrounding and defining a fluid chamber, the hollow component comprises a plurality of through holes located on the cylinder portion and connected to the fluid chamber; and
  at least one plate-shaped sensor embedded in the fluid chamber, wherein the hollow component comprises two guiding slots in the fluid chamber, and two opposite sides of the plate-shaped sensor are respectively directly positioned in the guiding slots;
  wherein, the hollow component is detachably plugged into the pipe, such that the at least one plate-shaped sensor is connected to the fluid channel through the plurality of through holes, and a diameter of each of the plurality of through holes and an inner diameter of the hollow component have a ratio between one-tenth and one-fifth;
  wherein the hollow component includes an opening at a distal end thereof exposing the plate-shaped sensor;
  wherein the plate-shaped sensor extends to the opening at the distal end of the hollow component and is exposed by the opening; and
  wherein a gap between two of the plurality of through holes adjacent to each other in the axial direction of the hollow component and a length of the cylinder portion have a ratio greater than one-tenth.

10. The sensing device according to claim 9, wherein the hollow component comprises a mounting portion connected to the cylinder portion in an axial direction of the hollow component, the mounting portion comprises a base part and a ring part, the ring part protrudes from the base part, the cylinder portion is connected to a side of the ring part opposite to the base part, the ring part comprises an outer surface and an external thread, the external thread is located on the outer surface, the pipe comprises an internal thread, the external thread is engaged with the internal thread so that the hollow component is fixed to the pipe.

11. The sensing device according to claim 9, wherein the hollow component comprises a mounting portion connected to the cylinder portion in an axial direction of the hollow component, the mounting portion comprises a base part and a ring part, the ring part protrudes from the base part, the cylinder portion is connected to a side of the ring part opposite to the base part, the ring part comprises an outer surface and at least one first fastening structure, the at least one first fastening structure is located on the outer surface, the pipe comprises at least one second fastening structure, the at least one first fastening structure is fixed to the at least one second fastening structure so that the hollow component is fixed to the pipe.

12. The sensing device according to claim 9, wherein the pipe includes a number of ports and the at least one plate-shaped sensor, the hollow component, and at least a portion of the plurality of through holes are positioned along an axis extending through at least two of the ports.

13. A sensing device, comprising:
  a pipe surrounding and defining a fluid channel;
  a hollow component surrounding and defining a fluid chamber, the hollow component comprises a plurality of through holes, and the plurality of the through holes connected to the fluid chamber; and
  at least one plate-shaped sensor embedded in the fluid chamber;
  wherein, the hollow component is detachably plugged into the pipe, such that the at least one plate-shaped sensor is connected to the fluid channel through the plurality of through holes, and a diameter of each of the plurality of through holes and an inner diameter of the hollow component have a ratio between one-tenth and one-fifth;
  wherein the hollow component includes an opening at a distal end thereof exposing the plate-shaped sensor: and
  wherein the hollow component comprises a cylinder portion and a mounting portion connected to each other in an axial direction of the hollow component, the cylinder portion surrounds the fluid chamber, the plurality of through holes are located on the cylinder portion, and a gap between two of the plurality of through holes adjacent to each other in the axial direction of the hollow component and a length of the cylinder portion have a ratio greater than one-tenth.

* * * * *